United States Patent
Kim et al.

(10) Patent No.: US 9,307,934 B2
(45) Date of Patent: Apr. 12, 2016

(54) MICRONEEDLE BIO-SAMPLING APPARATUS

(71) Applicant: Industry-Academic Cooperation Foundation, Chosun University, Gwangju (KR)

(72) Inventors: Youn-Tae Kim, Daejeon (KR); Ji-Hwan Lee, Jeollanam-do (KR); Jae-Hyo Jung, Gwangju (KR); Ji-Hoon Lee, Gwangju (KR)

(73) Assignee: Industry-Academic Cooperation Foundation, Chosun University (KR)

( * ) Notice: Subject to any disclaimer, the term of this patent is extended or adjusted under 35 U.S.C. 154(b) by 322 days.

(21) Appl. No.: 13/914,212

(22) Filed: Jun. 10, 2013

(65) Prior Publication Data
US 2014/0303519 A1 Oct. 9, 2014

(30) Foreign Application Priority Data
Apr. 9, 2013 (KR) .......................... 10-2013-0038739

(51) Int. Cl.
*A61B 5/15* (2006.01)
*A61B 5/151* (2006.01)

(52) U.S. Cl.
CPC ......... *A61B 5/1411* (2013.01); *A61B 5/150022* (2013.01); *A61B 5/15105* (2013.01); *A61B 5/15142* (2013.01); *A61B 5/150916* (2013.01); *A61B 5/150984* (2013.01); *A61B 5/150229* (2013.01); *A61B 5/150389* (2013.01); *A61B 5/150503* (2013.01)

(58) Field of Classification Search
CPC ............... A61B 5/144; A61B 5/15142; A61B 5/150885; A61B 5/150908; A61B 5/150916; A61B 5/15105; A61B 5/15113
See application file for complete search history.

(56) References Cited

U.S. PATENT DOCUMENTS

| 5,928,161 | A | 7/1999 | Krulevitch et al. | |
| 2005/0284757 | A1* | 12/2005 | Allen | 204/400 |
| 2012/0123297 | A1* | 5/2012 | Brancazio | 600/576 |

FOREIGN PATENT DOCUMENTS

WO WO 2012/000836 1/2012

* cited by examiner

*Primary Examiner* — Sean Dougherty
(74) *Attorney, Agent, or Firm* — The Farrell Law Firm, P.C.

(57) ABSTRACT

There is provided a microneedle bio-sampling apparatus including: an bio-sampling body enabling a microneedle to be inserted into human skin; and a blocking unit installed in the bio-sampling body and preventing the microneedle from moving to the skin again to prevent repeated bio-sampling by the microneedle. Since the microneedle bio-sampling apparatus is configured to prevent repeated bio-sampling of a single-use microneedle, secondary infection to other part of a human body or a different person due to blood, human anatomy, or the like, that may remain in a microneedle after the microneedle is used once otherwise in case of repeated bio-sampling of a microneedle, can be prevented.

6 Claims, 6 Drawing Sheets

MICRONEEDLE BIO-SAMPLING APPARATUS

PRIORITY

This application claims the priority of Korean Patent Application No. 10-2013-0038739 filed on Apr. 9, 2013, in the Korean Intellectual Property Office, the disclosure of which is incorporated herein by reference.

BACKGROUND OF THE INVENTION

1. Field of the Invention

The present invention relates to a microneedle bio-sampling apparatus and, more particularly, to a microneedle bio-sampling apparatus capable of preventing repeated bio-sampling by a single-use (or disposable) microneedle.

2. Description of the Related Art

In general, a pathological examination is an examination in which a tissue sample is removed from a patient's living body in order to diagnose a disease present therein, an important process in diagnosing and treating diseases in patients.

However, conventionally, large tissue samples have been taken from patients by using large living body inspection instruments, so large quantities of reagents have been required to analyze tissue samples. In addition, in conventional tissue-sampling methods, patients must endure a certain degree of pain and face risks in accordance with a surgical procedure.

As a solution to the existing problem, a microbiopsy/precision cutting device using a microfabrication process and a precision process has been proposed. This technique is disclosed in U.S. Pat. No. 5,928,161, entitled "Microbiopsy/Precision Cutting Devices" co-invented by Krulevithch, P., et al.

However, the microbiopsy/precision cutting device involves a relatively complicated biopsy process and requires an operator to be skilled in the technique of the use thereof, and can only perform a function of collecting a tissue sample, lacking the ability to perform a treatment function such as treating lesions in body tissue by injecting medication into the body tissue.

A general needle is used as an instrument for sampling an analysis material such as blood, or the like, for clinically diagnosing various diseases, obtaining a bio-sample from biological tissue, injecting medication into a living body, and the like. A majority of needles currently used for such purposes are microneedles having a millimeter-scale diameter, a very large diameter, relative to the size of a blood corpuscle (or cell). A diameter of a shaft of a microneedle may do serious damage to biological tissues while passing therethrough and cause pain in patients. The development of various diagnosis techniques and diagnosis chips to be applied to biological tissues has increased demand for detecting an analysis material from a living body, but the use of needles that may cause pain and inflict injuries on patients limits the use of various diagnosis technologies and equipment.

To address the limitations detailed above, microneedles having a micrometer-scale diameter have been proposed as an alternative and have been extensively employed for various purposes.

In particular, disease diagnosing devices for diagnosing diseases by collecting blood with a microneedle have been developed. In such disease diagnosing devices, a microneedle is used as a single-use product in order to eliminate the danger of secondary infection.

Namely, even though blood is collected once by disease diagnosing device using a microneedle, the occurrence of repeated bio-sampling due to user inadvertence may expose a patient to a risk of secondary infection due to blood remaining in the microneedle.

SUMMARY OF THE INVENTION

An aspect of the present invention provides a microneedle bio-sampling apparatus capable of preventing repeated bio-sampling by a single-use microneedle in order to prevent secondary infection due to repeated bio-sampling by the microneedle.

According to an aspect of the present invention, there is provided a microneedle bio-sampling apparatus including: a bio-sampling body enabling a microneedle to be inserted into human skin; and a blocking unit installed in the bio-sampling body and preventing the microneedle from moving to the skin again to prevent repeated bio-sampling by the microneedle.

The bio-sampling body may include: an external cover having a hollow having openings formed in both sides thereof; a pressing unit having one side in which the microneedle is installed and moving to skin along the hollow when pressed; and an elastic unit fixed to the external cover, connected to the pressing unit, and returning the pressing unit, which has been moved, to its original state when pressure applied thereto is removed.

The blocking unit may include: a film member fixed to the pressing unit and surrounding the microneedle; a film cover covering the film member and having a size corresponding to the edge of the pressing unit; and a blocking member fixed to the external cover to elastically press the film cover, and penetrating through the film member so as to extend inwardly of the film member when the film cover is released from its position, wherein the blocking member prevents the pressing unit from moving to the skin again to thus prevent repeated bio-sampling by the microneedle.

The blocking member may include: a spring fixedly fastened to the external cover and disposed within the external cover; a blocking bar connected to the spring and extending therefrom; and a flexible tube covering the spring and the blocking bar.

The pressing unit may include: an acupressure part protrusively exposed from one opening of the hollow before and after bio-sampling, and slidably guided along an inner circumferential surface of the hollow when moved; and a connection part having one side to which the acupressure part is fixed and the other side to which the microneedle is fixed.

The elastic unit may include: a support plate fastened to the external cover so as to be protruded inwardly, and limiting a movement of the pressing unit when pressure is applied to the pressing unit; and an elastic member connected to the pressing unit from the support plate to allow the pressing unit to reciprocate elastically with respect to the support plate.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
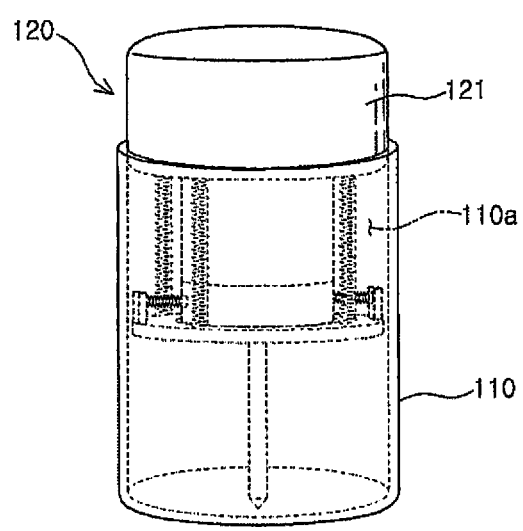
FIG. 1 is a perspective view of a microneedle bio-sampling apparatus according to an embodiment of the present invention.

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

A microneedle bio-sampling apparatus according to an embodiment of the present invention is configured to prevent repeated bio-sampling of a single-use microneedle, in order to prevent secondary infection to a part of a human body not affected by a disease or to a different person due to blood, human tissue, or the like, that may remain in a microneedle after the microneedle has been used once otherwise in the case of repeated bio-sampling by a microneedle.

Hereinafter, the microneedle bio-sampling apparatus according to an embodiment of the present invention will be described in detail with reference to the accompanying drawings.

Figure 2:
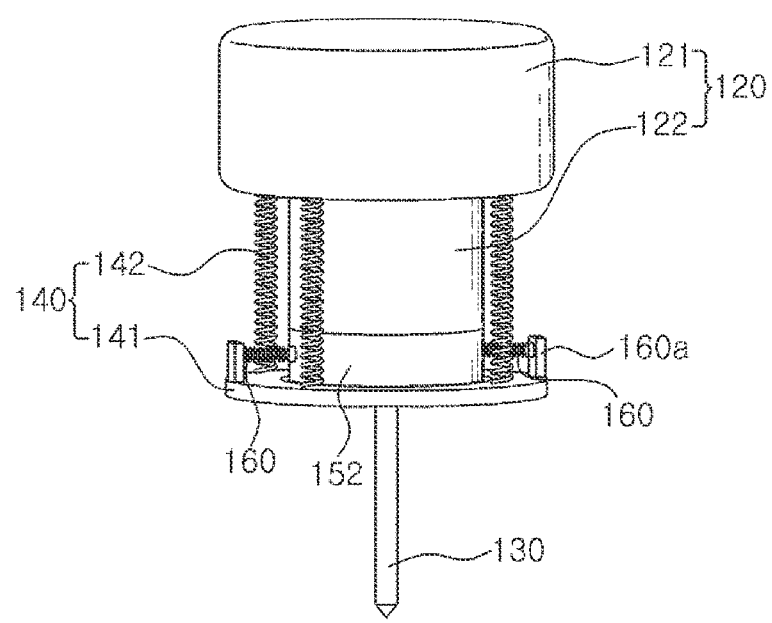
FIG. 2 is a perspective view of the microneedle bio-sampling apparatus of FIG. 1 without an external cover.

FIG. 1 is a perspective view of a microneedle bio-sampling apparatus according to an embodiment of the present invention, and FIG. 2 is a perspective view of the microneedle bio-sampling apparatus of FIG. 1 without an external cover.

Figure 3:
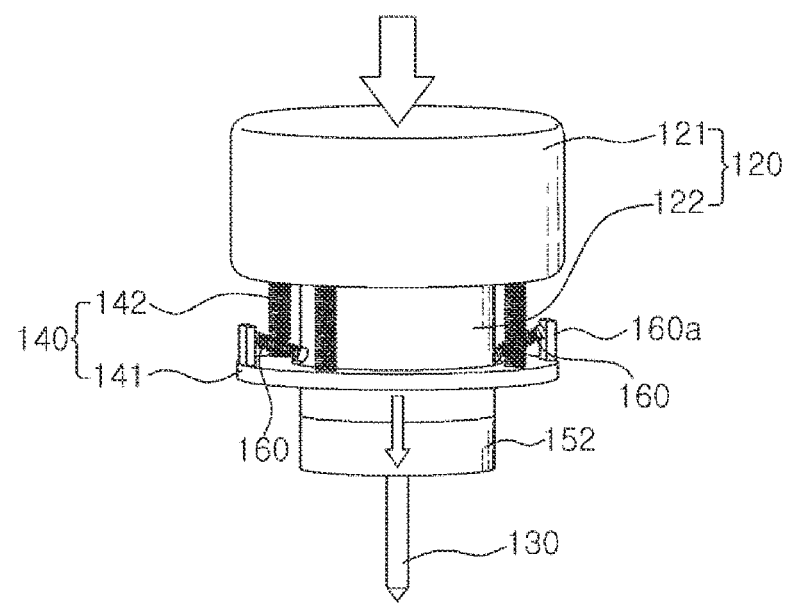
FIG. 3 is a perspective view of the microneedle bio-sampling apparatus of FIG. 2, in which a pressing unit is moved downwardly as pressure is applied thereto.
Figure 4:
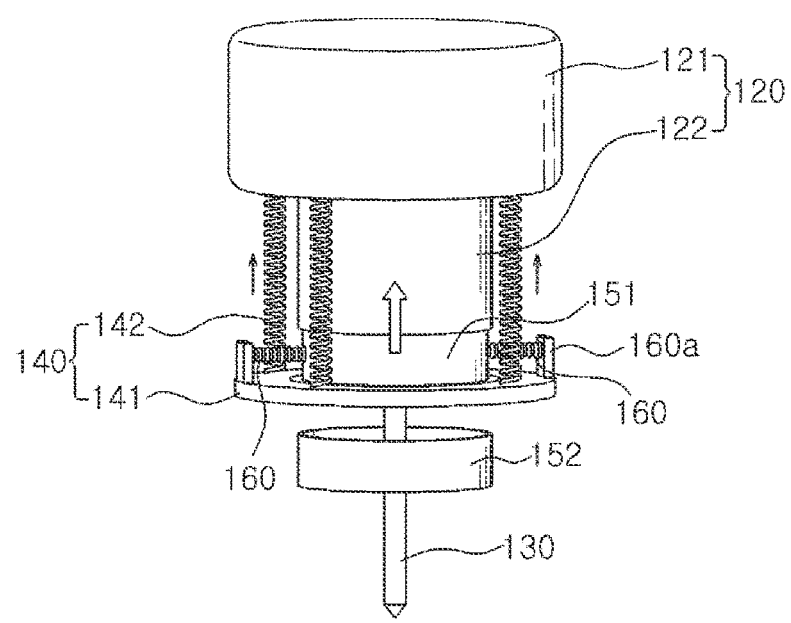
FIG. 4 is a perspective view of the microneedle bio-sampling apparatus of FIG. 3 in which the pressing unit is recovered upwardly as pressure applied to the pressing unit is released.

FIG. 3 is a perspective view of the microneedle bio-sampling apparatus of FIG. 2, in which a pressing unit is moved downwardly as pressure is applied thereto, and FIG. 4 is a perspective view of the microneedle bio-sampling apparatus of FIG. 3 in which the pressing unit is recovered upwardly as pressure applied to the pressing unit is released.

Figure 5:
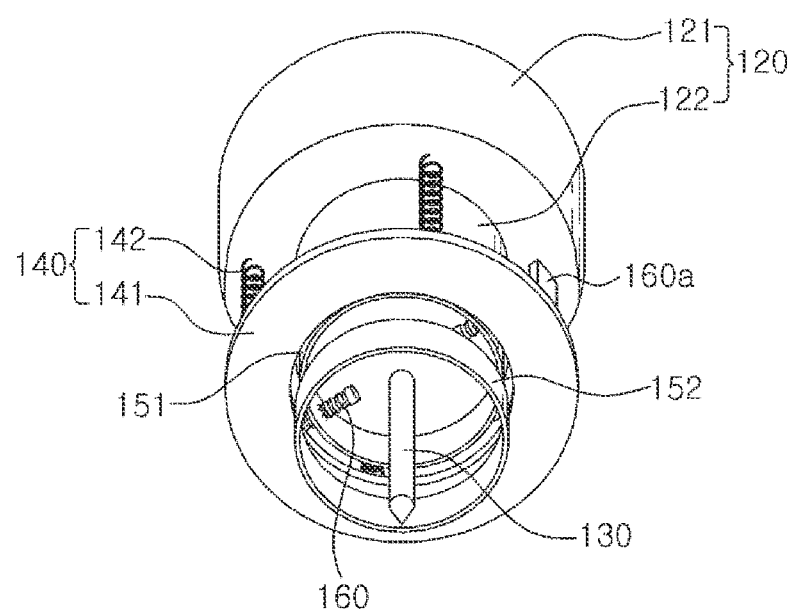
FIG. 5 is a perspective view of the microneedle bio-sampling apparatus of FIG. 4, in which a blocking member, penetrating through a film member, is moved inwardly from the film member.
Figure 6:
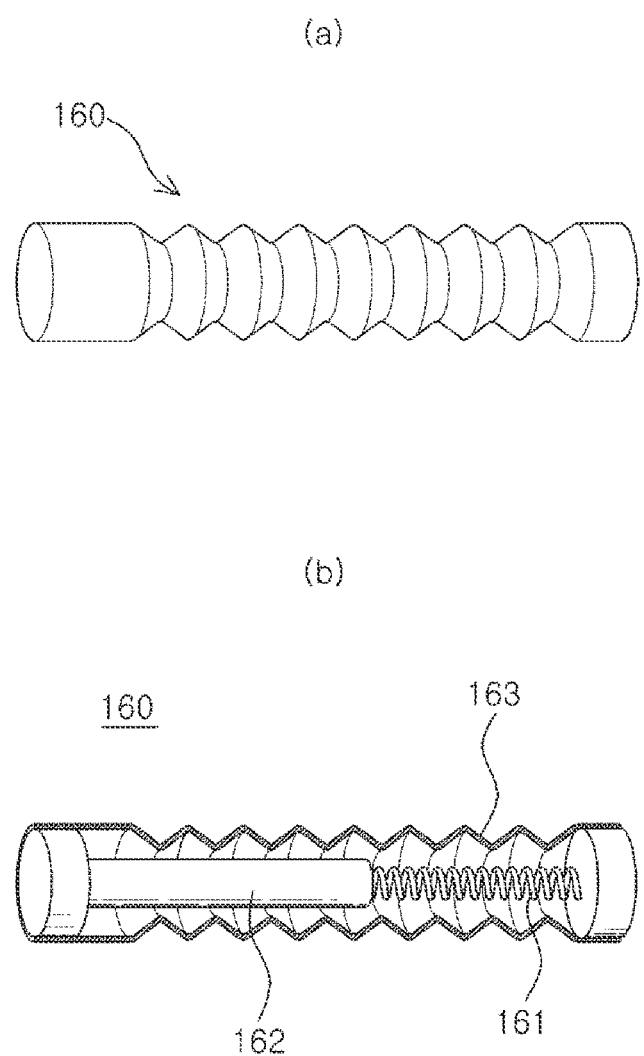
FIG. 6(a) is a perspective view of the blocking member of FIG. 5
FIG. 6(b) is a view illustrating the interior of the blocking member of FIG. 6(a).

FIG. 5 is a perspective view of the microneedle bio-sampling apparatus of FIG. 4, in which a blocking member, penetrating through a film member, is moved inwardly from the film member, and FIG. 6(a) is a perspective view of the blocking member of FIG. 5 and FIG. 6(b) is a view illustrating the interior of the blocking member of FIG. 6(a).

Referring to the drawings, the microneedle bio-sampling apparatus may include an bio-sampling body allowing a microneedle 130 to be inserted into skin and a blocking unit installed in the bio-sampling body to prevent repeated bio-sampling by the microneedle 130.

The bio-sampling body may serve to allow the microneedle 130 to be inserted into human skin. The bio-sampling body may include a hard external cover 110 and a pressing unit 120 and an elastic unit 140 disposed within the external cover 110.

The external cover 110 may have a hollow 110a having openings formed in both sides thereof. For example, in the microneedle bio-sampling apparatus disposed as illustrated in the drawings, openings are formed upper and lower portions, as both sides (two directions), of the microneedle bio-sampling apparatus. Hereinafter, an example in which the microneedle 130 is pressed downwardly to collect blood to diagnose the skin of a patient placed in a lower side based on the drawings will be described, based on this example, directions of components will be described.

The external cover 110 may be made of a hard material to withstand external impacts that may be applied thereto.

For reference, as illustrated, the external cover 110 may have a cylindrical shape and a circular cross-section. The pressing unit 120 disposed within the external cover 110 may have a circular cross-section to correspond to that of the external cover 110, but the present invention is not limited thereto and the cross-section of the external cover 110 may have an angular shape.

Also, the microneedle 130 is installed in one side of the pressing unit 120. The microneedle 30 is configured to move toward skin along the hollow 110a of the external cover 110 within the hollow 110a when pressure is applied thereto.

In detail, the pressing unit 120 may include an acupressure part 121 protrusively exposed from one opening of the hollow 110a of the external cover 110 before and after bio-sampling and a connection part 122 having one side to which the acupressure part 121 is fixed and the other side to which the microneedle 130 is fixed.

Here, without downward pressure, the acupressure part 121 may be disposed such that a predetermined portion thereof is exposed from the upper opening of the external cover 110. When a user presses the exposed portion of the acupressure part 121, downward pressure is applied to lower the acupressure part 121 by a predetermined length.

In addition, the acupressure part 121 may have a size corresponding to that of a sectional area of the hollow 110a so that, when moved, the acupressure part 121 may be slidably guided along an inner circumferential surface of the hollow 110a of the external cover 110.

In addition, the connection part 122 may be fixedly installed such that the acupressure part 121 is fixedly connected to an upper portion thereof and the microneedle 130 is disposed in a lower portion thereof.

Here, the microneedle 130 includes a hole formed to extend in a length direction therein and blood is drawn and collected through the hole. Although not shown, a suction pipe for drawing and collecting blood may communicate with the microneedle 130 and extend outwardly through the connection part 122 and the acupressure part 121, and a pumping member for sucking and a component for diagnosing collected blood may be connected to the suction pipe. Of course, the present invention is not limited to the microneedle 130, the suction component, and the diagnosing component, and any conventional configuration may also be utilized.

The elastic unit 140 may be fixed to the external cover 110 and connected to the pressing unit 120, serving to return the pressing unit 120, which has been moved, to its original state when pressure applied thereto is removed (or released).

In detail, the elastic unit 140 may include a support plate 141 fixedly fastened to the external cover 110 and an elastic member 142 connected to the pressing unit 120 from the support plate 141.

Here, the support plate 141 is fastened to the external cover 110 so as to be inwardly protruded, and serves to limit movement of the pressing unit 120 moving when pressure is applied thereto.

Namely, the acupressure part 121 of the pressing unit 120 corresponds to a horizontal sectional area of the cover, and the connection part 122 has a sectional area smaller than that of the acupressure part 121. Since the support plate 141 has a circular band shape, when the pressing unit 120 is moved downwardly, the connection part 122 may pass through a central passage of the support plate 141 while the acupressure part 121 is caught by the support plate 141, being limited in movement.

In this manner, since the support plate 141 limits movement of the pressing unit 120 which moves when pressure is applied thereto, the microneedle 130 may only be inserted into a patient's skin to a predetermined depth.

Also, the elastic member 142 is connected to the pressing unit 120 from the support plate 141 such that the pressing unit 120 can reciprocate elastically with respect to the support plate 141.

Namely, a lower end portion of the elastic member 142 is fixed to an upper surface of the support plate 141 and an upper end portion thereof is fixed to a lower surface of the acupressure part 121 of the pressing unit 120, so that when pressure is applied to the pressing unit 120, the elastic member 142 is compressed, and when applied pressure is released, the elastic member 142 moves the pressing unit 120 upwardly by elastic force thereof to return the pressing unit 120 to its original state.

Meanwhile, the blocking unit is installed in the bio-sampling body and configured to prevent the microneedle 130 from being moved again to a skin to prevent repeated bio-sampling by the microneedle 130. This will be described with reference to FIGS. 3 through 6.

In detail, the blocking unit may include a film member 151 fixed to the pressing unit 120 and surrounding the microneedle 130, a film cover 152 covering the film member 151, and a blocking member 160 elastically pressing an outer circumferential surface of the film cover 152.

Here, the film member 151 may be fixed to a lower surface of the pressing unit 120 and extended downwardly, having a band-like shape. The film member 151 may be made of a thin film such as a membrane so as to be penetrated by elastic compression of the blocking member 160 as described hereinafter.

Also, the film cover 152 has a structure covering the film member 151. This is to prevent the blocking member 160 from penetrating though the film member 151.

The film cover 152 may have a size corresponding to the edges of the pressing unit 120. This allows the blocking member 160, which elastically presses the outer circumferential surface of the film cover 152, to be easily slidably moved to the outer circumferential surface of the pressing unit 120 positioned above the film cover 152, when the pressing unit 120 and the film cover 152 are moved downwardly according to pressure applied to the pressing unit 120.

The blocking member 160 may be fixed to the external cover 110 to elastically press the outer circumferential surface of the film cover 152 to fix the film cover 152 in position to cover the film member 151.

When the pressing unit 120, which has moved toward a patient's skin, is returned to its original state, elastic compression of the blocking member 160 with respect to the film cover 152 is released, allowing the film cover 152 to be separated from the film member 151.

Here, the blocking member 160, elastically pressing the outer circumferential surface of the film member 151, penetrates through the film member 151 so as to be extendedly disposed inwardly of the film member 151 to prevent re- movement of the pressing unit 120 toward the skin, thus preventing repeated bio-sampling by the microneedle 130.

The blocking member 160 may include a spring 161 fixedly fastened to the external cover 110 so as to be disposed on an inner side of the external cover 110, a blocking bar 162 connected to the sprig 161 and extending therefrom, and a flexible tube 163 covering the spring 161 and the blocking bar 162. For reference, the blocking member 160 and the external cover 110 may be connected by a connection block 160a.

Here, when the blocking member 160 is released from a state of supporting the film cover 152 through elastic force, the spring 161 is in contact with the film member 151 and simultaneously penetrates through the film member 151 so as to be extendedly disposed inwardly of the film member 151.

The spring 161 extending to the inner side of the film member 151 is flexible in terms of maintaining a shape thereof, so it cannot completely prevent the pressing unit 120 from moving again toward the skin. Thus, the hard blocking bar 162 is connected to an end portion of the spring 161 and disposed in a downward movement path of the pressing unit 120 to interfere with the pressing unit 120, whereby a downward re-movement of the pressing unit 120 can be reliably prevented.

Also, the flexible tube 163 covers and protects the spring 161 and the blocking bar 162, and a degree of folding thereof may be adjusted according to elasticity (or stretch) of the spring 161 to correspond to a change in the length of the spring 161.

Operation order of the microneedle bio-sampling apparatus according to an embodiment of the present invention configured as described above will be described with reference to FIGS. 2 through 5.

First, in order to allow the microneedle 130 to be inserted into a patient's skin, the user presses the acupressure part 121 of the pressing unit 120 as illustrated in FIG. 3.

Accordingly, the microneedle 130 installed under the pressing unit 120 is moved downwardly to be primarily inserted into a user's skin, and during this process, the blocking member 160 elastically pressing the film cover 152 moves to the connection part 122 of the downwardly moved pressing unit 120 as illustrated in FIG. 2.

Subsequently, when pressure applied to the pressing unit 120 is removed or released, the microneedle 130 is released together with the pressing unit 120 from the skin by virtue of elastic force of the elastic member 142 and moves upwardly.

At this time, since elastic compression of the blocking member 160 with respect to the film cover 152 covering the film member 151 is released, position fixing force with respect to a position covering the film member 151 is gone, and thus, the film member 151 remains on the lower side due to the weight thereof, rather than moving upwardly, as illustrated in FIG. 4.

At the same time, as illustrated in FIG. 5, as the internal spring 161 of the blocking member 160 comes into contact with the film member 151, it penetrates through the film member 151 to extend to the inner side of the film member 151.

In this manner, the blocking member 160, extending to the inner side of the film member 151, is disposed in a downward movement path of an extended portion of the pressing unit 120. Thus, even in the case that the pressing unit 120 is pressed by the user again, so as to be moved downwardly, the blocking member 120 blocks the pressing unit 120, thus preventing repeated bio-sampling by the microneedle 130 to the skin.

Thus, since repeated bio-sampling of the single-use microneedle 130 is prevented, a non-diseased part of a human body or a different person is prevented from being secondarily infected by blood, human tissue, or the like, that may remain in the microneedle 130 due to repeated bio-sampling by the microneedle 130 after the microneedle 130 is used once.

As set forth above, according to embodiments of the invention, the microneedle bio-sampling apparatus is configured to prevent repeated bio-sampling of a single-use microneedle. Therefore, secondary infection to other part of a human body or a different person due to blood, human anatomy, or the like, that may remain in a microneedle after the microneedle is used once otherwise in case of repeated bio-sampling of a microneedle, can be prevented.

While the present invention has been shown and described in connection with the embodiments, it will be apparent to those skilled in the art that modifications and variations can be made without departing from the spirit and scope of the invention as defined by the appended claims.

What is claimed is:

1. A bio-sampling apparatus comprising:
    a bio-sampling body configured to enable insertion of a needle into a sample; and
    a blocking unit installed in the bio-sampling body,
    wherein the blocking unit is configured to prevent the needle from repeatedly moving into the sample,
    wherein the bio-sampling body comprises:
        an external cover having a hollow connecting openings formed in a plurality of sides of the external cover;
        a pressing unit having one side in which the needle is installed, wherein the pressing unit is configured to move toward the sample along the hollow; and
        an elastic unit fixed to the external cover, connected to the pressing unit,
    wherein the elastic unit returns the pressing unit, having moved toward the sample, to an original state of the pressing unit when pressure applied to the pressing unit is removed,
    wherein the blocking unit comprises:
        a film member fixed to the pressing unit and surrounding the needle;
        a film cover covering the film member and having a size corresponding to an edge of the pressing unit; and
        a blocking member fixed to the external cover and configured to elastically press the film cover, penetrating through the film member to extend inwardly when the film cover is removed from a position covering the film member, and
    wherein the blocking member prevents the pressing unit from repeatedly moving toward the sample, thereby preventing repeated bio-sampling.

2. The apparatus of claim 1, wherein the blocking member comprises:
    a spring fixedly fastened to the external cover and disposed within the external cover;
    a blocking bar connected to the spring and extending from the spring; and
    a flexible tube covering the spring and the blocking bar.

3. The apparatus of claim 1, wherein the pressing unit comprises:
    an acupressure part protrusively exposed from one opening connecting the hollow before and after bio-sampling, and slidably guided along an inner circumferential surface of the hollow when moved; and
    a connection part having one side to which the acupressure part is fixed and the other side to which the needle is fixed.

4. The apparatus of claim 1, wherein the elastic unit comprises:
    a support plate fastened to the external cover so as to be protruded inwardly from the external cover, and limiting a movement of the pressing unit to prevent the pressing unit from moving beyond a position of the support plate when pressure is applied to the pressing unit; and
    an elastic member connected to the pressing unit from the support plate to allow the pressing unit to reciprocate elastically with respect to the support plate.

5. The apparatus of claim 2, wherein the elastic unit comprises:
    a support plate fastened to the external cover so as to be protruded inwardly of the external cover, and limiting a movement of the pressing unit to prevent the pressing unit from moving beyond a position of the support plate when pressure is applied to the pressing unit; and
    an elastic member connected to the pressing unit from the support plate to allow the pressing unit to reciprocate elastically with respect to the support plate.

6. The apparatus of claim 3, wherein the elastic unit comprises:
    a support plate fastened to the external cover so as to be protruded inwardly of the external cover, and limiting a movement of the pressing unit to prevent the pressing unit from moving beyond the position of the support plate when pressure is applied to the pressing unit; and
    an elastic member connected to the pressing unit from the support plate to allow the pressing unit to reciprocate elastically with respect to the support plate.

* * * * *